United States Patent [19]

Tominago et al.

[11] Patent Number: 4,737,501
[45] Date of Patent: Apr. 12, 1988

[54] SUBSTITUTED PIPERAZINYL OXINDOL COMPOUNDS AND CARDIOTONIC COMPOSITIONS CONTAINING THE SAME

[75] Inventors: Michiaki Tominago; Hidenori Ogawa; Takafumi Fujioka; Kazuyuki Nakagawa, all of Tokushima, Japan

[73] Assignee: Otsuka Pharmaceutical Co., Ltd., Tokyo, Japan

[21] Appl. No.: 751,849

[22] Filed: Jul. 5, 1985

[30] Foreign Application Priority Data

Jul. 6, 1984 [JP] Japan .................................. 59-141254
Jul. 6, 1984 [JP] Japan .................................. 59-141255
Jul. 6, 1984 [JP] Japan .................................. 59-141256

[51] Int. Cl.$^4$ .................. A61K 31/495; C07D 209/12; C07D 403/02
[52] U.S. Cl. .................. 514/253; 514/252; 544/373; 544/377
[58] Field of Search ............. 544/373, 374, 377; 514/252, 253

[56] References Cited

U.S. PATENT DOCUMENTS 3,462,450  8/1969  Shen .................................. 548/486
4,415,572  11/1983  Tominaga et al. .................. 514/252

FOREIGN PATENT DOCUMENTS 337170  7/1974  Austria .
40539  9/1983  Japan .
169461  9/1985  Japan .................................. 544/373

OTHER PUBLICATIONS

Offermanns et al., Chem. Abst. 81-105570m, eg. DE 2360.545.
Nishi et al., Chem. Abst. 88-62293y, eg. JP 118464/1977.
Beilsteins Handbuck Der Organischen Chemie, 1953.
Beilsteins Handbuch Der Organischen Chemie, 1935.
Derwent abstract 45693V, Dt 2360-545(6-12-74).
Derwent abstract 10251 B/06, ep. 485 (2-7-79).

Primary Examiner—Donald G. Daus
Assistant Examiner—Cecilia Shen
Attorney, Agent, or Firm—Finnegan, Henderson, Farabow, Garrett & Dunner

[57] ABSTRACT

An oxindol compound of the formula (I)

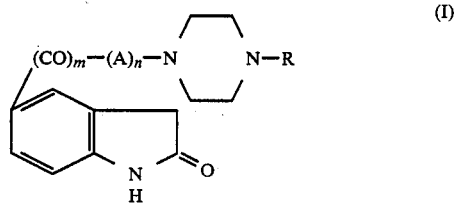

wherein

A represents a lower alkylene group;

R represents a hydrogen atom, a lower alkyl group, a phenyl-lower alkyl group, a phenoxy-lower alkyl group, a benzoyl-lower alkyl group, a lower alkoxycarbonyl group, a lower alkanoyl group, a benzoyl group which may be substituted with 1 to 3 of a lower alkyl group, a lower alkoxy group and a halogen atom on the benzene ring thereof, or a benzoyl group which is substituted with a lower alkylenedioxy group on the benzene ring thereof; and m and n, which may be the same or different, each represents an integer of 0 or 1, with proviso that when n is an integer of 1, then m is an integer of 1, when A is an ethylene group and m is an integer of 1, then R should not be 3,4,5-trimethoxybenzoyl group, and when A is a group of the formula: —C(R$^1$)(R$^2$)—(where R$^1$ and R$^2$ are, the same or different, a hydrogen atom or a lower alkyl group) and m is an integer of 1, then R should not be a hydrogen atom; or its pharmaceutically acceptable salt, composition containing the compound and processes for preparing the same are disclosed.

The compound is useful as a cardiotonic agent.

25 Claims, No Drawings

SUBSTITUTED PIPERAZINYL OXINDOL COMPOUNDS AND CARDIOTONIC COMPOSITIONS CONTAINING THE SAME

BACKGROUND OF THE INVENTION

This invention relates to certain oxindol compounds and to pharmaceutically acceptable salts thereof which are useful as cardiotonic agents, processes for preparing the same, and pharmaceutical compositions containing the oxindol compounds or salt thereof.

Various oxindol compounds are known which have hypotensive, blood platelet coagulation inhibitory, anti-inflammatory or anti-ischemic activity as described in Japanese Patent Publication (examined) No. 40539/1983, U.S. Pat. No. 3462450, Austrian Patent Application No. 10443/72 and Swiss Patent Application No. 8483/77.

However, the oxindol compounds of this invention are structurally different from the conventional oxindol compounds.

SUMMARY OF THE INVENTION

One object of this invention is to provide oxindol compounds having a cardiotonic activity.

Another object of this invention is to provide a pharmaceutical composition containing the oxindol compound in a cardiotonically effective amount.

A further object of this invention is to provide a process for preparing the oxindol compound and its pharmaceutically acceptable salts thereof.

As a result of extensive research this invention has been accomplished which, in one aspect, provides an oxindol compound of the formula (I):

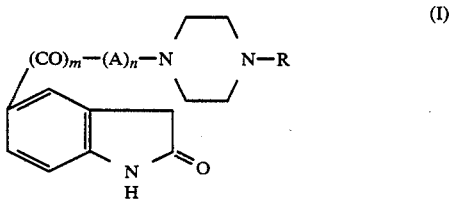

wherein

A represents a lower alkylene group;

R represents a hydrogen atom, a lower alkyl group, a phenyl-lower alkyl group, a phenoxy-lower alkyl group, a benzoyl-lower alkyl group, a lower alkoxycarbonyl group, a lower alkanoyl group, a benzoyl group which may be substituted with 1 to 3 of a lower alkyl group, a lower alkoxy group and a halogen atom on the benzene ring thereof, or a benzoyl group which is substituted with a lower alkylenedioxy group on the benzene ring thereof; and m and n, which may be the same or different, each represents an integer of 0 or 1, with proviso that when n is an integer of 1, then m is an integer of 1, when A is an ethylene group and m is an integer of 1, then R should not be 3,4,5-trimethoxybenzoyl group, and when A is a group of the formula: —C(R$^1$)(R$^2$)—(-where R$^1$ and R$^2$ are, the same or different, a hydrogen atom or a lower alkyl group) and m is an integer of 1, then R should not be a hydrogen atom; or its pharmaceutically acceptable salt.

In another aspect, this invention provides a cardiotonic composition containing a compound of the formula (I) or a pharmaceutically acceptable salt thereof in a cardiotonically effective amount.

In a further aspect, this invention provides processes for preparing the compounds of the formula (I) and pharmaceutically acceptable salts thereof.

The compounds of the formula (I) above and pharmaceutically acceptable salts thereof have heart muscle contraction stimulating effect or positive inotropic effect and coronary blood flow increasing activity, and are useful as a cardiotonic agent for treating heart diseases such as congestive heart failure and the like. They are advantageous in that they do not or only slightly, if any, increase heart beats.

As to the object compound of the formula (I), the following point is to be noted. That is, the "oxindol" moiety in the object compound of the formula (I) can be alternatively represented by its tautomer i.e. "2-hydroxyindole", and both of said moieties are in the state of tautomeric equilibrium as represented by the following scheme.

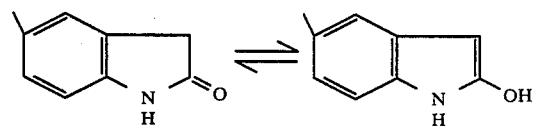

This tautomerism has been well known in the arts, and it is obvious to a person skilled in the arts that both of the tautomeric isomers are equilibrated and lie in the reciprocally convertible state. In the present specification, however, the object compound of the invention including the group of such tautomeric isomers is represented by one of the expressions, i.e. "oxindol" and the formula:

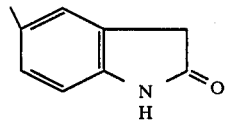

only for the convenient sake.

DETAILED DESCRIPTION OF THE INVENTION

The term "lower alkylene" as used herein refers to a straight or branched chain alkylene group having 1 to 6 carbon atoms such as a methylene group, an ethylene group, a propylene group, a trimethylene group, a 2-methyltrimethylene group, a 2,2-dimethyltrimethylene group, a 1-methyltrimethylene group, a methylmethylene group, an ethylmethylene group, a tetramethylene group, a pentamethylene group, a hexamethylene group and the like.

The term "lower alkyl" as used herein refers to a straight or branched chain alkyl group having 1 to 6 carbon atoms such as a methyl group, an ethyl group, a propyl group, an isopropyl group, a butyl group, a tert-butyl group, a pentyl group, a hexyl group and the like.

The term "phenyl-lower alkyl" as used herein refers to a phenyl-lower alkyl group having a straight or branched chain alkyl group having 1 to 6 carbon atoms in the alkyl moiety such as a benzyl group, a 2-phenylethyl group, a 1-phenylethyl group, a 3-phenylpropyl group, a 4-phenylbutyl group, a 1,1-dimethyl-2- phenylethyl group, a 5-phenylpentyl group, a 6-phenylhexyl group, a 2-methyl-3-phenylpropyl group and the like.

The term "phenoxy-lower alkyl" as used herein refers to a phenoxy-lower alkyl group having a straight or branched chain alkyl group having 1 to 6 carbon atoms in the alkyl moiety such as a phenoxymethyl group, a 1-phenoxyethyl group, a 2-phenoxyethyl group, a 1-phenoxypropyl group, a 2-phenoxypropyl group, 3-phenoxypropyl group, a 2-methyl-3-phenoxypropyl group, a 4-phenoxybutyl group, a 5-phenoxypentyl group, a 6-phenoxyhexyl group and the like.

The term "benzoyl-lower alkyl" as used herein refers to a benzoyl-lower alkyl group having a straight or branched chain alkyl group having 1 to 6 carbon atoms in the alkyl moiety such as a benzoylmethyl group, a 1-benzolylethyl group, a 2-benzoylethyl group, a 1-benzoylpropyl group, a 3-benzoylpropyl group, a 4-benzoylbutyl group, a 5-benzoylpentyl group, a 6-benzoylhexyl group, a 1,1-dimethylbenzoylethyl group, a 2-methylbenzoylpropyl group and the like.

The term "lower alkoxycarbonyl" as used herein refers to a straight or branched chain alkoxycarbonyl group having 1 to 6 carbon atoms in the alkoxy moiety such as a methoxycarbonyl group, an ethoxycarbonyl group, a propoxycarbonyl group, an isopropoxycarbonyl group, a butoxycarbonyl group, a tert-butoxycarbonyl group, a pentyloxycarbonyl group, a hexyloxycarbonyl group and the like.

The term "lower alkanoyl" as used herein refers to a straight or branched chain alkanoyl group having 1 to 6 carbon atoms such as a formyl group, an acetyl group, a propionyl group, a butyryl group, an isobutyryl group, a pentanoyl group, a pivaloyl group, a hexanoyl group and the like.

The term "lower alkoxy" as used herein refers to a straight or branched chain alkoxy group having 1 to 6 carbon atoms such as a methoxy group, an ethoxy group, a propoxy group, an isopropoxy group, a butoxy group, a tert-butoxy group, a pentyloxy group, a hexyloxy group and the like.

The term "halogen" as used herein refers to fluorine, chlorine, bromine and iodine.

The term "lower alkylenedioxy" as used herein refers to a straight or branched chain alkylenedioxy group having 1 to 4 carbon atoms such as a methylenedioxy group, an ethylenedioxy group, a trimethylenedioxy group and the like.

The term "benzoyl group which may be substituted with 1 to 3 of a lower alkyl group, a lower alkoxy group and a halogen atom on the benzene ring thereof" as used herein refers to a benzoyl group which may be substituted with 1 to 3 of a straight or branched chain alkyl group having 1 to 6 carbon atoms, a straight or branched chain alkoxy group havin 1 to 6 carbon atoms and a halogen atom such as a benzoyl group, a 2-methylbenzoyl group, a 3-methylbenzoyl group, a 4-methylbenzoyl group, a 2-ethylbenzoyl group, a 3-ethylbenzoyl group, a 4-ethylbenzoyl group, a 3-isopropylbenzoyl group, a 4-hexylbenzoyl group, a 3,4-dimethylbenzoyl group, a 2,5-dimethylbenzoyl group, a 3,4,5-trimethylbenzoyl group, a 2-methoxybenzoyl group, a 3-methoxybenzoyl group, a 4-methoxybenzoyl group, a 2-ethoxybenzoyl group, a 3-ethoxybenzoyl group, a 4-ethoxybenzoyl group, a 4-isopropoxybenzoyl group, a 4-hexyloxybenzoyl group, a 3,4-dimethoxybenzoyl group, a 3,4-diethoxybenzoyl group, a 3,4,5-trimethoxybenzoyl group, a 2,5-dimethoxybenzoyl group, a 2-chlorobenzoyl group, a 3-chlorobenzoyl group, a 4-chlorobenzoyl group, a 2-fluorobenzoyl group, a 3-fluorobenzoyl group, a 4-fluorobenzoyl group, a 2-bromobenzoyl group, a 3-bromobenzoyl group, a 4-bromobenzoyl group, a 2-iodobenzoyl group, a 4-iodobenzoyl group, a 3,5-dichlorobenzoyl group, a 2,6-dichlorobenzoyl group, a 3,4-dichlorobenzoyl group, a 3,4-difluorobenzoyl group, a 3,5-dibromobenzoyl group, a 3,4,5-trichlorobenzoyl group, a 3-methyl-4-chlorobenzoyl group, a 2-chloro-6-methylbenzoyl group, a 2-methoxy-3-chlorobenzoyl group and the like.

The term "benzoyl group which is substituted with a lower alkylenedioxy group on the benzene ring thereof" as used herein refers to a benzoyl group substituted with straight or branched chain alkylenedioxy group having 1 to 4 carbon atoms on the benzene ring thereof such as a 3,4-methylenedioxybenzoyl group, a 3,4-ethylenedioxybenzoyl group, a 2,3-methylenedioxybenzoyl group, a 3,4-propylenedioxybenzoyl group, a 3,4-tetramethylenedioxybenzoyl group and the like.

The compounds of this invention of the formula (I) can be prepared by various alternative procedures. A preferred example thereof is a process according to Reaction Scheme-1 below.

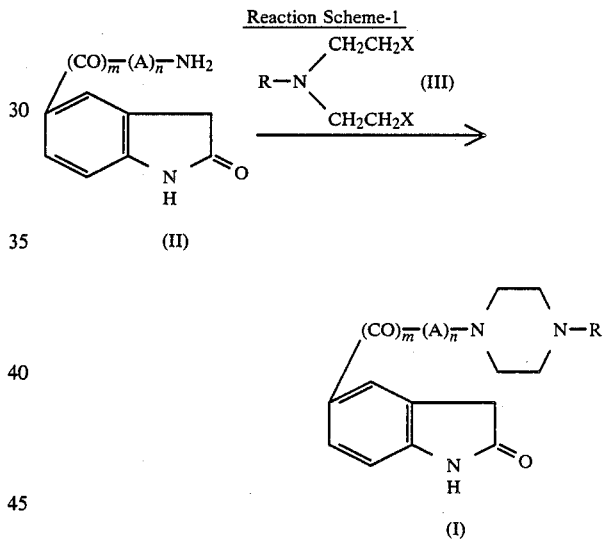

In the above formulae, X represents a halogen atom, a lower alkanesulfonyloxy group, an arylsulfonyloxy group, an aralkylsulfonyloxy group or a hydroxy group; and R, A, m and n have the same meanings as defined above.

In the formula (III), examples of the halogen atom represented by X include chlorine, fluorine, bromine and iodine; examples of the low alkanesulfonyloxy group represented by X include a methanesulfonyloxy group, an ethanesulfonyloxy group, an isopropanesulfonyloxy group, a propanesulfonyloxy group, a butanesulfonyloxy group, a tert-butanesulfonyloxy group, a pentanesulfonyloxy group, a hexanesulfonyloxy group and the like; examples of the arylsulfonyloxy group represented by X include a substituted or unsubstiuted arylsulfonyloxy group such as a phenylsulfonyloxy group, a 4-methylphenylsulfonyloxy group, a 2-methylphenylsulfonyloxy group, a 4-nitrophenylsulfonyloxy group, a 4-methoxyphenylsulfonyloxy group, a 3-chlorophenylsulfonyloxy group, a 1-naphthylsulfonyloxy group and the like; and examples of the aralkylsulfonyloxy group represented by X include a substituted or unsubstituted aralkylsufonyloxy group such as a benzylsulfonyloxy group, a 2-phenylethylsulfonyloxy group, a 4-phenylbutylsulfonyloxy group, a 4-methylbenzylsulfonyloxy group, a 2-methylbenzylsulfonyloxy group, a 2-nitrobenzylsulfonyloxy group, a 4-methoxybenzylsulfonyloxy group, a 3-chlorobenzylsulfonyloxy group, a 1-naphthylmethylsulfonyloxy group and the like.

In the case where, of the compounds of the formula (III), those in which X represents a halogen atom, a lower alkanesulfonyloxy group, an arylsulfonyloxy group or an aralkylsulfonyloxy group are used as a starting material, the reaction between the known compound of the formula (II) and the known compound of the formula (III) can be carried out generally in a suitable inert solvent in the presence or absence of a basic condensing agent.

Examples of the suitable inert solvent which can be used include aromatic hydrocarbons such as benzene, toluene, xylene and the like, lower alcohols such as methanol, ethanol, isopropyl alcohol, butanol and the like, acetic acid, ethyl acetate, dimethyl sulfoxide, dimethylformamide, hexamethylphosphoric triamide and the like.

Examples of the basic condensing agent include carbonates such as sodium carbonate, potassium carbonate, sodium hydrogencarbonate, potassium hydrogencarbonate and the like, metal hydroxides such as sodium hydroxide, potassium hydroxide and the like, metal alcoholates such as sodium methylate, sodium ethylate and the like, tertiary amines such as pyridine, triethylamine and the like.

In the above reaction, the proportion of the compound of the formula (III) to the compound of the formula (II) is not particularly limited, and can be varied broadly. Usually the reaction is carried out using at least an equimolar amount, and preferably from 1 to 5 mols, of the compound of the formula (III) per mol of the compound of the formula (II). The reaction can be carried out usually at about 40° to 120° C., preferably 50° to 100° C., and completed generally in about 5 to 30 hours.

On the other hand, in the case where, of the compounds of the formula (III), that in which X represents a hydroxy group is used as a starting material, the reaction between the compound of the formula (II) and the compound of the formula (III) can be carried out in the presence of a dehydrating-condensing agent without solvents or in a suitable solvent.

Examples of the dehydrating-condensing agent include condensed phosphoric acids such as polyphosphoric acid and the like, phosphoric acids such as orthophosphoric acid, pyrophosphoric acid, metaphosphoric acid and the like, phosphorus acids such as orthophosphorus acid and the like, phosphoric anhydrides such as phosphorus pentoxide and the like, inorganic acids such as hydrochloric acid, sulfuric acid, boric acid and the like, metal phosphates such as sodium phosphate, boron phosphate, ferric phosphate, aluminum phosphate and the like, activated alumina, sodium hydrogensulfate, Raney nickel and the like.

As for the solvent, high boiling point solvents such as dimethylformamide, tetralin and the like can be used.

In the above reaction, the proportion of the compound of the formula (III) to the compound of the formula (II) is not particularly limited, and can be varied broadly. Usually, the reaction is carried out using at least an equimolar amount, and preferably 1 to 2 mols, of the compound of the formula (III) per mol of the compound of the formula (II).

The amount of the dehydrating-condensing agent is not particularly limited, and can be varied broadly. Usually, at least a catalytic amount, preferably 0.5 to 5 mols, of the dehydrating-condensing agent per mol of the compound of the formula (II) is used.

Preferably, the above reaction is carried out in a stream of an inert gas such as carbon dioxide, nitrogen in order to prevent oxidation reaction which is undesirable.

The reaction can be carried out either at atmospheric pressure or under pressure. Preferably, the reaction is carried out at atmospheric pressure.

The reaction can proceed advantageously usually at about 100° to 350° C., preferably 125° to 255° C. and completed generally in about 3 to 10 hours.

It should be noted that the compound of the formula (III) can be used in form of its salt.

Of the compound of the formula (I), those in which R represents a lower alkoxycarbonyl group, a lower alkanoyl group, a benzoyl group which may be substituted with 1 to 3 of a lower alkyl group, a lower alkoxy group and a halogen atom on the benzene ring thereof, or a benzoyl group which is substituted with a lower alkylenedioxy group on the benzene ring thereof; and A, m and n have the same meanings as defined above, can be prepared according to the Reaction Scheme-2 below.

Reaction Scheme-2

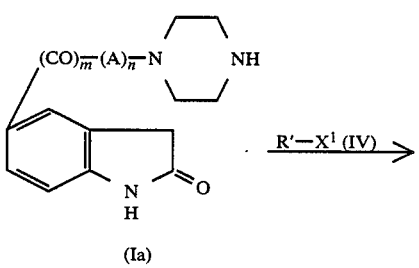

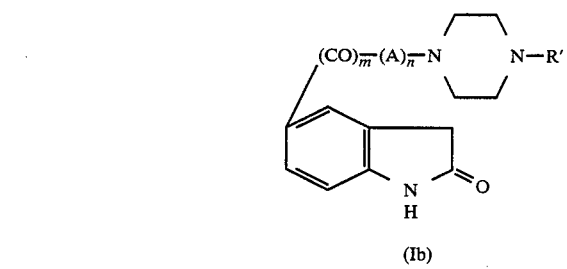

In the above formulae, R' represents a lower alkoxycarbonyl group, a lower alkanoyl group, a benzoyl group which may be substituted with 1 to 3 of a lower alkyl group, a lower alkoxy group and a halogen atom on the benzene ring thereof, or a benzoyl group which is substituted with a lower alkylenedioxy group on the benzene ring thereof; $X^1$ represents a hydroxy group; and A, m and n have the same meanings as defined above.

The process shown in Reaction Scheme-2 above is a reaction between an oxindol derivative of the formula (Ia) and a carboxylic acid of the formula (IV) using a conventional amido formation reaction. The process can readily be achieved with applying conditions for known amido formation reaction. Representative examples of the processes include:

(a) Mixed Acid Anhydride Process

The compound of the formula (IV) is reacted with an alkyl haloformate to form mixed acid anhydride thereof which is then reacted with an amine of the formula (Ia).

(b) Activated Ester Process

The carboxylic acid compound of the formula (IV) is converted into a reactive ester such as a p-nitrophenyl ester, an N-hydroxy-succinimide ester, a 1-hydroxybenzotriazole ester, etc., which is then reacted with an amine of the formula (Ia).

(c) Carbodiimide Process

The carboxylic acid compound of the formula (IV) and an amine of the formula (Ia) are condensed in the presence of an activating agent such as dicyclohexylcarbodiimide, carbonyldiimidazole, etc.

(d) Other Process

The carboxylic acid compound of the formula (IV) is converted into an acid anhydride using a dehydrating agent such as acetic anhydride, etc., followed by reacting the product with an amine of the formula (Ia); process in which the lower alcohol ester of the carboxylic acid compound of the formula (IV) is reacted with an amine of the formula (Ia) at a high temperature under pressurized conditions; the carboxylic acid compound of the formula (IV) is converted into an acid halide using a halogenating agent followed by reacting the product with an amine of the formula (Ia); or the carboxylic acid compound of the formula (IV) is converted into its activated form using phosphorus compounds such as triphenylphosphine, diethylchlorophosphate and the like followed by reacting the product with an amine of the formula (Ia).

In the mixed acid anhydride process, the mixed acid anhydrides can be prepared in accordance with conventional Schötten-Baumann reaction and subjected further to reaction with the amine of the formula (Ia) without isolation to give the compound of the formula (Ib).

The Schötten-Baumann reaction can be carried out in the presence of a basic compound. As for the basic compound, any conventional basic compound conventionally used in Schötten-Baumann reaction can be used. Examples of suitable basic compounds include organic bases such as triethylamine, trimethylamine, pyridine, N,N-dimethylaniline, N-methylmorpholine, 4-dimethylaminopyridine, 1,5-diazabicyclo[4,3,0]nonene-5 (DBN), 1,8-diazabicyclo[5,4,0]undcene-7 (DBU), 1,4-diazabicyclo[2,2,2]octane (DABCO) and the like, inorganic bases such a potassium carbonate, sodium carbonate, potassium hydrogencarbonate, sodium hydrogencarbonate and the like.

The reaction can proceed at about $-20°$ to $100°$ C., preferably $0°$ to $50°$ C. and continued for about 5 minutes to 10 hours, preferably 5 minutes to 2 hours.

The reaction between the mixed acid anhydride and the amine of the formula (Ia) can proceed at about $-20°$ to $150°$ C., preferably $10°$ to $50°$ C. for about 5 minutes to 10 hours, preferably 5 minutes to 5 hours.

The mixed acid anhydride process can proceed in the absence or presence of a solvent. As for the solvent any solvent used conventionally in the mixed acid anhydride processes can be used. Examples of suitable solvents include halogenated hydrocarbons such as methylene chloride, chloroform, dichloroethane and the like, aromatic hydrocarbons such as benzene, toluene, xylene and the like, ethers such as diethyl ether, tetrahydrofuran, dimethoxyethane and the like, esters such as methyl acetate, ethyl acetate and the like, and aprotic polar solvents such as N,N-dimethylformamide, dimethyl sulfoxide, hexamethylphosphoric triamide and the like.

Examples of suitable alkyl haloformate which can be used in the mixed acid anhydride process include methyl chloroformate, methyl bromoformate, ethyl chloroformate, ethyl bromoformate, isobutyl chloroformate and the like.

In the above reaction, the alkyl haloformate and the carboxylic acid compound of the formula (IV) is used usually, at least about 1 mol, preferably 1 to 2 mols, relative to the amine of the formula (Ia).

The activated ester process (b), when using N-hydroxysuccinimide ester for example, is carried out in a suitable solvent which does not influence the reaction. Examples of suitable solvents include halogenated hydrocarbons such as methylene chloride, chloroform, dichloroethane and the like, aromatic hydrocarbons such as benzene, toluene, xylene and the like, ethers such as diethyl ether, tetrahydrofuran, dimethoxyethane and the like, esters such as methyl acetate, ethyl acetate and the like, aprotic polar solvents such as N,N-dimethylformamide, dimethyl sulfoxide, hexamethylphosphoric triamide and the like. The reaction is completed at temperatures of $0°$ to $150°$ C., preferably $10°$ to $100°$ C., in 5 to 30 hours. The N-hydroxysuccinimide ester is used at least 1 mol preferably 1 to 2 mols per mol of the amine of the formula (Ia).

On the other hand, the reaction between the carboxylic acid halide and the amine of the formula (Ia) can be carried out in an appropriate solvent in the presence of a dehydrohalogenation agent. As for the dehydrohalogenation agent various known basic compounds can be used. For example, sodium hydroxide, potassium hydroxide, sodium hydride, potassium hydride and the like, in addition to the basic compounds used in the above Schötten-Baumann reaction can be used. Examples of suitable solvents include, in addition to those used in the above Shoötten-Baumann reaction, alcohols such as methanol, ethanol, propanol, butanol, 3-methoxy-1-butanol, ethyl cellosolve, methyl cellosolve and the like, pyridine, acetone, acetonitrile and the like.

Proportion of the carboxylic acid halide to the amine of the formula (Ia) is not limited but can be varied widely. Usually, at least 1 mol, preferably 1 to 5 mols, of the carboxylic acid halide per mol of the amine of the formula (Ia) is used.

The reaction can proceed usually at $-30°$ to $180°$ C., preferably $0°$ to $150°$ C. and completed generally in 5 minutes to 30 hours.

The process in which a carboxylic acid of the formula (IV) activated with a phosphorus compound such as triphenylphosphine and diethylchlorophosphate is reacted with an amine of the formula (Ia) is carried out in a suitable solvent. Any solvent which does not influence the reaction can be used. Examples of suitable solvents include halogenated hydrocarbons such as methylene chloride, chloroform, dichloroethane and the like, aromatic hydrocarbons such as benzene, toluene, xylene and the like, ethers such as diethyl ether, tetrahydrofuran, dimethoxyethane and the like, esters such as methyl acetate, ethyl acetate and the like, and aprotic polar solvents such as N,N-dimethylformamide, dimethyl sulfoxide, hexamethylphosphoric triamide and the like. The reaction is preferably carried out in the presence of a base, for example, organic bases such as triethylamine, pyridine, dimethylaniline, N-methylmorpholine, DBN, DBU, DABCO and the like, and inorgaic baes such as potassium carbonate, sodium carbonate, potassium bicarbonate, sodium bicarbonate and the like. The reaction proceeds at temperatures from about 0° to 150° C., preferably from 0° to 100° C., for about 1 to 30 hours. The phosphorus compound is used usually at least one mol, preferably 1 to 3 mols per mol of the carboxylic acid of the formula (IV).

Of the compounds of the formula (I), those in which R represents a lower alkyl group, a phenyl-lower alkyl group, a phenoxy-lower alkyl group or a benzoyl-lower alkyl group, and A, m and n have the same meanings as defined above, can be prepared according to Reaction Scheme-3 below.

Reaction Scheme-3

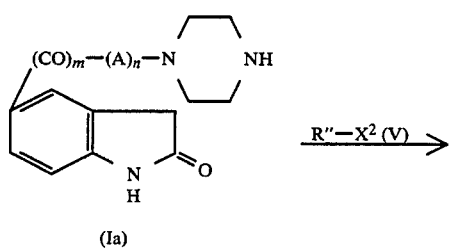

In the above formulae, R" represents a lower alkyl group, a phenyl-lower alkyl group, a phenoxy-lower alkyl group or a benzoyl-lower alkyl group; $X^2$ represents a halogen atom, a lower alkanesulfonyloxy group, an arylsufonyloxy group or aralkylsulfonyloxy group; and A, m and n have the same meanings as defined above.

The reaction between the compound of the formula (Ia) and the compound of the formula (V) can be carried out under conditions similar to those used in the reaction between the compound of the formula (Ia) and the carboxylic acid halide above.

Of the compounds of the formula (I), those in which m is an integer of 1, n is an integer of 0, and R has the same meaning as defined above, can be prepared according to Reaction Scheme-4 below.

Reaction Scheme-4

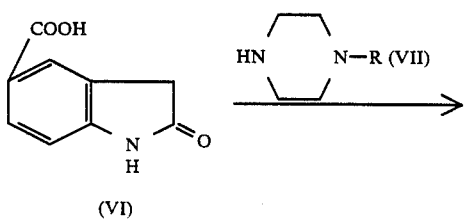

-continued
Reaction Scheme-4

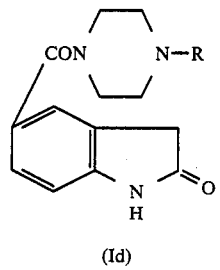

In the above formulae, R has the same meaning as defined above.

The reaction between the compound of the formula (VI) and the compound of the formula (VII) can be carried out under conditions similar to those used in the reaction between the compound of the formula (Ia) and the carboxylic acid of the formula (IV) above.

Of the compounds of the formula (I), those in which both of m and n are an integer of 1, and R and A have the same meanings as defined above, can be prepared according to Reaction Scheme-5 below.

Reaction Scheme-5

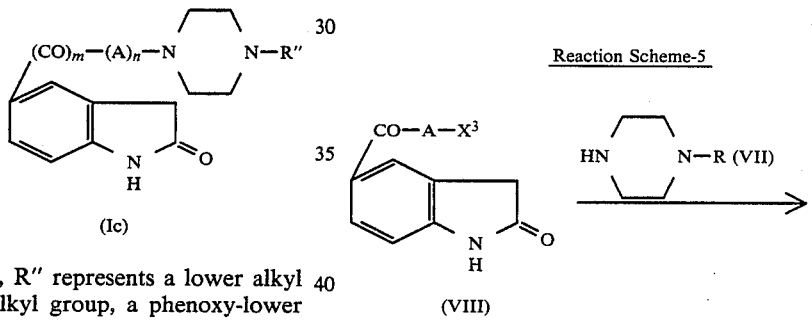

In the above formulae, $X^3$ represents a halogen atom, and R and A have the same meanings as defined above.

The reaction between the compound of the formula (VIII) and the compound of the formula (VII) can be carried out under conditions similar to those used in the reaction between the compound of the formula (Ia) and the carboxylic acid halide above.

The compound of the formula (VI) used in the preparation of a compound of the formula (Id) in the Reaction Scheme-4 detailed above is useful as an intermediate and has a cardiotonic activity per se and can be prepared, for example, by the processes shown in the following Reaction Scheme-6 or 7:

Reaction Scheme-6

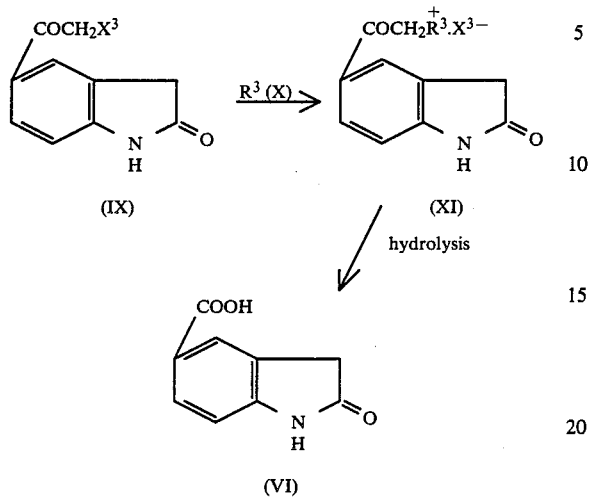

In the above formulae, $X^3$ has the same meaning as defined above and $R^3$ represents an aromatic amine group.

A compound of the formula (XI) is obtained by the reaction of a compound of the formula (IX) and an aromatic amine (X) in the absence or presence of a suitable solvent. As for the solvent, any solvent that exerts no influence on the reaction can be used here. Examples of the suitable solvent include halogenated hydrocarbons such as methylene chloride, chloroform, dichloroethane and the like, esters such as diethyl ether, tetrahydrofuran, dimethoxyethane and the like, esteres such as methyl acetate, ethyl acetate and the like, aprotic polar solvents such as N,N-dimethylformamide, dimethylsulfoxide, hexamethylphosphoric triamide and the like. Examples of the aromatic amine include pyridine, quinoline and the like. The aromatic amine is used at least equimolar, preferably in a great excess amount to the amount of the compound of the formula (IX). The reaction can proceed usually at about 50° to 200° C., preferably 70° to 150° C., and the reaction is completed generally in 1 to 10 hours. The hydrolysis of the compound of the formula (XI) obtained above can be carried out in water or an alcohol such as methanol, ethanol and the like, in the presence of an inorganic base such as sodium hydroxide, potassium hydroxide and the like or an acid such as hydrochloric acid, hydrobromic acid and the like, at room temperature to 150° C. and the reaction is completed generally in 10 minutes to 10 hours.

Reaction Scheme-7

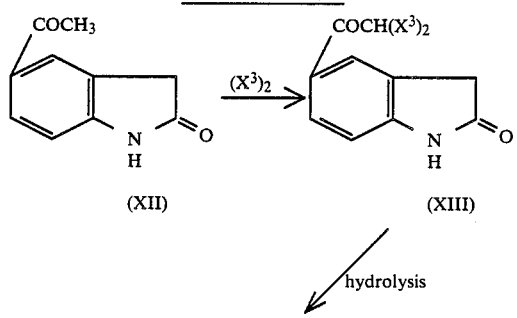

-continued
Reaction Scheme-7

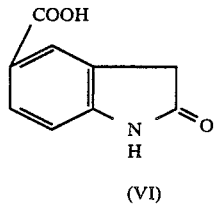

In the above formulae, $X^3$ has the same meaning as defined above.

The reaction of a compound of the formula (XII) and a halogen is usually carried out in a solvent. Examples of the solvent include ethers such as tetrahydrofuran, dioxan and the like, carboxylic acids such as acetic acid, propionic acid and the like, aromatic hydrocarbons such as benzene, xylene, toluene and the like, dimethylformamide, dimethyl sulfoxide and the like. In the reaction, a deacidifying agent such as calcium carbonate and the like may be added to remove the hydrogen halide produced as by-product. The proportion of a compound of the formula (XII) to the halogen is not particularly limited and can be varied broadly. Usually the reaction is carried out using 2 to 5 mols, preferably 2 to 3 mols, of the halogen per mol of the compound of the formula (XII). The reaction can be carried out usually at 0° to 50° C., and completed in several to 24 hours.

The hydrolysis of the compound of the formula (XIII) into the compound of the formula (VI) is carried out preferably in water in the presence of a basic compound. Known basic compounds in wide range can be used. They are, for example, alkali metal hydroxides such as sodium hydroxide, potassium hydroxide and the like or alkaline earth metal hydroxides such as calcium hydroxide and the like. The amount of the basic compound to be used is not particularly limited and can be varied broadly. Preferably, from two mols to a great excess amount of the basic compound per mol of the compound of the formula (XIII) is used. The hydrolysis can be carried out usually at 50° to 150° C., preferably at 70° to 120° C., and completed generally in about 1 to 12 hours.

The compound of the formula (VIII) used for the preparation of a compound of the formula (Ie) in the Reaction Scheme-5 includes partly novel compound, and is prepared, for example, according to the process shown in the following Reaction Scheme-8.

Reaction Scheme-8

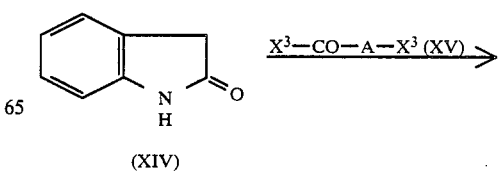

-continued
Reaction Scheme-8

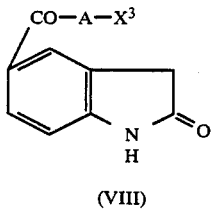

(VIII)

In the above formulae, A and $X^3$ have the same meanings as defined above.

The reaction of oxindol of the formula (XIV) and a compound of the formula (XV) is generally called "Friedel-Crafts reaction", and usually carried out in a solvent in the presence of a Lewis acid. As for the solvent, any solvent to be commonly used in this reaction, for example, carbon disulfide, nitrobenzene, chlorobenzene, dichloromethane, dichloroethane, trichloroethane, tetrachloroethane and the like can be used. Any Lewis acid conventionally used can be used favarably; for example, aluminum chloride, zinc chloride, iron chloride, tin chloride, boron tribromide, concentrated sulfuric acid and the like. The amount of the Lewis acid to be used is not particularly limited, and can be varied broadly. Usually, 2 to 6 mols, preferably 2 to 4 mols of the Lewis acid per mol of the oxindol of the formula (XIV) is used. The compound of the formula (XV) is usually used at least 1 mol, preferably 1 to 2 mols per mol of the oxindol of the formula (XIV). The reaction temperature can be selected appropriately, but usually 0° to 120° C., preferably 0° to 70° C. is used. The reaction time cannot be absolutely mentioned being dependent on the raw materials, catalyst, reaction temperature and the like, but usually the reaction is completed in 0.5 to 6 hours.

A compound used in the invention of which R is a hydrogen atom can be obtained from a compound of which R is a phenyl-lower alkyl group or a lower alkanoyl group by dephenyl(lower)alkylation or de(lower)alkanoylation, respectively.

The dephenyl(lower)alkylation can be carried out under the conditions of ordinary de-N-phenyl(lower)alkylation reaction. The reaction can be carried out in a suitable solvent in the presence of a reduction catalyst such as palladium-carbon, palladium black and the like, at 0° C. to room temperature, in about 0.5 to 3 hours. The solvent to be used is, for example, water, lower alcohols such as methanol, ethanol, isopropanol and the like, ethers such as dioxane, tetrahydrofuran and the like, acetic acid and the like.

The de(lower)alkanoylation reaction is carried out in a similar manner to the ordinary hydrolysis, for example, in water or an alcohol such as methanol, ethanol and the like, in the presence of an inorganic base such as sodium hydroxide, potassium hydroxide and the like or an acid such as hydrochloric acid, hydrobromic acid and the like.

The dephenyl(lower)alkylation can be also carried out under similar conditions to those of the de(lower)alkanoylation mentioned above.

The compounds of this invention represented by the formula (I) prepared as described above can form pharmaceutically acceptable salts with acids and this invention also includes within its scope such pharmaceutically acceptable salts. The pharmaceutically acceptable acids which can be used for the salt formation can be various inorganic acids, for example, hydrochloric acid, sulfuric acid, phosphoric acid, hydrobromic acid, organic acids such as oxalic acid, maleic acid, fumaric acid, malic acid, tartaric acid, citric acid, benzoic acid and the like.

The compounds of the formula (VI) can be converted into a pharmaceutically acceptable base addition salt by reacting the acid group with a pharmaceutically acceptable basic compound. Examples of the basic compounds are inorganic basic compounds such as sodium hydroxide, potassium hydroxide, calcium hydroxide, sodium carbonate, potassium hydrogencarbonate and the like.

The compounds of the formula (I) and the salts thereof obtained as described above can be isolated from the respective reaction mixtures upon completion of the reaction and purified by conventional procedures, for example, solvent extraction, dilution method, precipitation, recrystallization, column chromatography, preparative thin layer chromatography and the like.

As is apparent to those skilled in the art, the compounds of the formula (I) can exist in optically active forms and this invention includes such optical isomers within its scope.

In using the compounds of this invention of the formula (I) and the salts thereof as therapeutic agents, these compounds can be formulated into pharmaceutical compositions together with ordinary pharmaceutically acceptable carriers. Suitable carriers which can be used are, for example, solvents, wetting agents, disintegrants, surface active agents and lubricants which are usually employed to prepare such drugs depending on the type of dosage form.

Various dosage forms of the therapeutic agents as a cardiotonic agent can be selected according to the purpose of the therapy. Typical dosage forms which can be used are tablets, pills, powders, liquid preparations, suspensions, emulsions, granules, capsules, suppositories, and injectable preparations (solutions, suspensions and the like).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dired starch, sodium alginate, agar powder, laminaria powder, sodium hydrogencarbonate, calcium carbonate, Tween, sodium laurylsulfate, stearic acid monoglyceride, starch, and lactose, disintegration inhibitors such as white sugar, stearic acid glyceryl ester, cacao butter and hydrogenated oils, adsorption promotors such as quaternary ammonium bases and sodium laurylsulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a cardiotonic agent, in an amount sufficient to prepare isotonic solutions. The cardiotonic agent may further contain ordinary dissolving aids, buffers, painalleviating agents, and preservatives, and optionally coloring agents, perfumes, flavors, sweeteners, and other drugs.

The amount of the compound of the formula (I) and the pharmaceutically acceptable salts thereof of this invention as an active ingredient to be incorporated into a pharmaceutical composition useful as a cardiotonic agent is not particularly limited, and can vary over a wide range. A suitable therapeutically effective amount of the compound of the general formula (I) and the pharmaceutically acceptable salts thereof of this invention is usually about 1 to about 70% by weight, preferably 1 to 30% by weight, based on the entire composition.

The administration method of the cardiotonic agent according to the invention is not particularly limited and can be adequately selected according to the form of the preparation, age and sex of the patient, and symptom of disease. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the cardiotonic agent can be singly administered intramuscularly, intracutaneously, subcutaneously, or intraperitoneally. The suppository is administered intrarectally.

The dosage of the cardiotonic agent is suitably selected according to the purpose of use, the symptoms and the like. Usually, a preferred dosage of the compound of this invention is about 0.1 to 10 mg/kg weight per day. It is advantageous that the active ingredient is contained in a single unit dose form in an amount of 1 to 200 mg.

Hereinafter, this invention will be described in greater detail with reference to Reference Examples, Examples and Preparation Examples.

REFERENCE EXAMPLE 1

5-Chloroacetyloxindol (45 g) was added to 180 ml of pyridine and the mixture was stirred at 80° C. for an hour. After completion of reaction, the mixture was allowed to cool and crystals which precipitated were collected by filtration and washed with acetone. The crystals were then recrystallized from methanol to give 5-α-pyridinumacetyloxindolchloride.

The compound was added to 600 ml of water containing 12.7 g of sodium hydroxide and stirred at 70°–80° C. for 30 minutes. After completion of reaction, the resultant solution was allowed to cool down and acidified with concentrated hydrochloric acid. Crystals which precipitated were collected by filtration and washed with water. The crystals were then recrystallized from a mixture of dimethylformamide (DMF) and water to give 28 g of 5-carboxyoxindol.

m.p.: >300° C.

Colorless powdery crystal

| Elemental analyses for $C_9H_7O_3N$ | | | |
|---|---|---|---|
| | C | H | N |
| Calc'd (%) | 61.01 | 3.98 | 7.90 |
| Found (%) | 61.12 | 3.81 | 8.10 |

REFERENCE EXAMPLE 2

α-Chloroacetyl chloride (47.4 g) and 80.0 g of finely-ground anhydrous aluminum chloride were suspended in 100 ml of carbon bisulfide under ice-cooling. Oxindol (26.6 g) was added thereto with vigorous stirring and the mixture was refluxed for about 3 hours. Then the solvent was removed under reduced pressure, and the residue was poured into 1 l of ice-water and allowed to cool for a while. Crystals which precipitated were collected by filtration, washed successively with water, methanol, and diethyl ether, and dried to give 15 g of 5-(α-chloroacetyl)oxindol.

m.p.: 246.5°–247.0° C.

EXAMPLE 1

A mixture of 5-aminooxindol (14 g), 29 g of bis(β-bromoethyl)amine.hydrobromide in 250 ml of ethanol was stirred under reflux for 8 hours and allowed to stand overnight at room temperature. To the mixture was added sodium carbonate (10.1 g) and the mixture was stirred further for 8 hours under reflux. After cooling to room temperature, crystals which precipitated were collected by filtration and recrystallized from a mixture of water and ethanol to give 16 g of 5-(1-piperazinyl)oxindol.hydrobromide.

Pale yellow powdery crystal

NMR (200 MHz, DMSO-$d_6$) δ: 3.30 (8H, s), 3.47 (2H, s), 6.78 (1H, d, J=8.5 Hz), 6.90 (1H, dd, J=8.5 Hz, 2 Hz), 7.04 (1H, d, J=2 Hz), 8.88 (2H, brs), 10.27 (1H, s)

Mass. M+: 217

In an analogous manner as Example 1, the compounds shown in Table 1 were prepared using appropriate starting materials.

TABLE 1

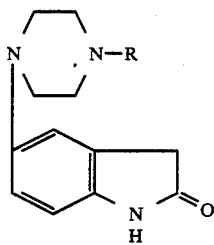

| Example | R | Crystal Form (Recrystallization solvent) | m.p. (°C.) |
| --- | --- | --- | --- |
| 2 | —CO—⟨benzene⟩(OCH₃)(OCH₃) | Yellow powdery crystal (methanol) | 197–199 |
| 3 | —CO—⟨benzene⟩(OCH₃)(OCH₃)(OCH₃) | Pale purple powdery crystal (isopropyl alcohol) | 216–217.5 |
| 4 | —CO—⟨benzene⟩—OC₂H₅ | Pale purple scales (isopropyl alcohol) | 175–176 |
| 5 | —CO—⟨benzene⟩—CH₃ | Pale reddish yellow needles (isopropyl alcohol) | 205.5–207.5 |
| 6 | —CO₂C₂H₅ | Purple needles (isopropyl alcohol) | 173–174 |
| 7 | —CH₂—⟨benzene⟩ | Pale yellowish green granules (isopropyl alcohol) | 202–203 |

EXAMPLE 8

5-(1-Piperazinyl)oxindol.hydrobromide (2.0 g) was suspended in 30 ml of N,N-dimethylformamide (DMF), and 2.3 ml of triethylamine was added thereto subsequently. The mixture was cooled to 0° to 5° C. To the mixture was added dropwise 5 ml of DMF solution containing 1.5 g of 3,4-dimethoxybenzoyl chloride at the same temperature as above with stirring. After completion of addition, the mixture was stirred at room temperature for one hour. The reaction mixture was poured into a large amount of water and extracted with chloroform. After washing with water, the extract was dried over anhydrous sodium sulfate and chloroform was removed by distillation. The residue was purified by silica-gel column chromatography (eluent: chloroform:methanol=100:1) and recrystallized from methanol to give 1.5 g of 5-[4-(3,4-dimethoxybenzoyl)-1-piperazinyl]oxindol.

m.p.: 197°–199° C.

Yellow powdery crystal

EXAMPLE 9

In an analogous manner as Example 8, the same compounds as those obtained in Examples 3 to 6 were prepared using appropriate starting materials.

EXAMPLE 10

A mixture of 5-(1-piperazinyl)oxindol.hydrobromide (1.0 g), 1.2 g of benzyl chloride and 1.1 g of triethylamine in 20 ml of acetonitrile was stirred at room temperature for 6 hours. The reaction mixture was poured into a large amount of water and extracted with chloroform. After washing with water, the extract was dried over anhydrous sodium sulfate and chloroform was removed. The residue was recrystallized from isopropyl alcohol to give 0.7 g of 5-(4-benzyl-1-piperazinyl)oxindol.

m.p.: 202°–203° C.

Pale yellowish green granules

EXAMPLE 11

A mixture of 5-aminooxindol.hydrobromide (3.8 g), 5.9 g of N,N-(di-2-hydroxyethyl)-3,4-dimethoxybenzamide and 8.6 g of 85% phosphoric acid was stirred at 165° to 175° C. for 4.5 hours and allowed to cool to room temperature. To the reaction mixture was added 50 ml of water. The resultant mixture was neutralized with 48% aqueous sodium hydroxide solution and extracted with chloroform. After drying over potassium carbonate, chloroform was evaporated. The residue was recrystallized from methanol to give 4.1 g of 5-[4-(3,4-dimethoxybenzoyl)-1-piperazinyl]oxindol.

m.p.: 197°–199° C.

Yellow powdery crystal.

EXAMPLE 12

In an analogous manner as Example 11, the same compounds as those obtained in Examples 1 and 3 to 7 above were prepared using appropriate starting materials.

EXAMPLE 13

3,4-Dimethoxybenzoic acid (2.6 g) and 1.65 g of 1,8-diazabicyclo[5,4,0]undecene-7 were added to 100 ml of DMF and to the mixture was added dropwise 1.5 ml of isobutyl chloroformate with ice-cooling externally with stirring. After completion of addition, the mixture was stirred for 30 minutes. To the mixture was added 40 ml of DMF solution containing 2.16 g of 5-(1-piperazinyl)oxindol and the mixture was stirred at room temperature for 5 hours. After completion of reaction, the solvent was removed by distillation. The residue was extracted with 300 ml of chloroform and the extract was washed with a diluted aqueous solution of sodium hydrogencarbonate, water, diluted hydrochloric acid and water, successively. Chloroform was removed by distillation and the residue was recrystallized from methanol to give 1.6 g of 5-[4-(3,4-dimethoxybenzoyl)-1-piperazinyl]oxindol.

m.p.: 197°–199° C.

Yellow powdery crystal

EXAMPLE 14

In an analogous manner as Example 13, the same compounds as those obtained in Examples 3 to 6 were prepared using appropriate starting materials.

EXAMPLE 15

To a solution of 0.88 g of 5-carboxyoxindol in 10 ml of DMF was added under ice-cooling 0.82 ml of triethylamine, and 0.77 ml of isobutyl chloroformate was added thereto subsequently. The mixture was stirred at the same temperature for 1 hour. Then, 1.1 g of 1-benzylpiperazine was added thereto, and the mixture was stirred at room temperature overnight. After the reaction was completed, DMF was removed under reduced pressure, and to the residue was added an aqueous sodium hydrogencarbonate solution and extracted with chloroform. After washing with water and drying over magnesium sulfate, chloroform was distilled off under reduced pressure. The resultant residue was purified by silica-gel column chromatography (eluent: methylene chloride:methanol=50:1) and recrystallized from isopropyl alcohol to give 0.7 g of 5-(4-benzyl-1-piperazinylcarbonyl)oxindol.

m.p.: 151°-153° C.

Colorless prisms

In an analogous manner as Example 5, the compounds shown in Table 2 were prepared using appropriate starting materials.

rated saline solution, and dried over anhydrous magnesium sulfate. Dichloromethane was distilled off, and the residue was purified by silica-gel column chromatography (eluent: methylene chloride:methanol=50:1). By recrystallization from isopropyl alcohol, 0.3 g. of 5-(4-acetyl-1-piperazinylcarbonyl)oxindol was obtained.

m.p.: 181°-182° C.

Colorless powdery crystal

EXAMPLE 24

In an analogous manner as Example 23, the same compound as that obtained in Example 18 was prepared using appropriate starting materials.

TABLE 2

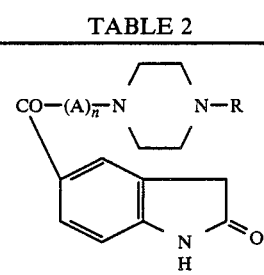

| Example | n | R | Crystal Form (Recrystallization solvent) | m.p. (°C.) | Salt |
|---|---|---|---|---|---|
| 16 | 0 | H | Colorless powder | 293-296 (decomposed) | HCl |
| 17 | 0 | —COCH$_3$ | Colorless powdery crystal (isopropyl alcohol) | 181-182 | — |
| 18 | 0 | —CO—C$_6$H$_5$ | Colorless prisms (methanol) | 268-270 | — |
| 19 | 0 | —(CH$_2$)$_2$C(O)—C$_6$H$_5$ | Colorless prisms (methanol-dichloromethane) | 208-210 | — |
| 20 | 0 | —(CH$_2$)$_5$—O—C$_6$H$_5$ | Colorless prisms (ethanol-water) | 245-248 (decomposed) | HCl |
| 21 | 0 | —CH$_2$CH(CH$_3$)$_2$ | Colorless needles (ethanol-methanol) | 285-289 (decomposed) | HCl |
| 22 | 0 | —(CH$_2$)$_2$—O—C$_6$H$_5$ | Colorless needles (ethanol-water) | 249-252 (decomposed) | HCl |

EXAMPLE 23

5-(1-Piperazinylcarbonyl)oxyindol hydrochloride (1.0 g) was suspended in 20 ml of dichloromethane, and then 1.32 ml of triethylamine was added thereto, and the mixture was stirred for 10 minutes under ice-cooling. Then, 0.3 ml of acetyl chloride was added thereto and the mixture was stirred further for 30 minutes at the same temperature. After completion of reaction, the solvent was distilled off under reduced pressure, and to the residue was added water and made alkaline with sodium carbonate. The mixture was extracted with dichloromethane, washed with water and with a satu-

EXAMPLE 25

A mixture of 0.8 g of β-chloropropiophenone, 1.0 g of sodium iodide and 20 ml of acetone was refluxed for 1 hour. After the solvent was distilled off, to the residue were added 10 ml of DMF, 1.0 g of 5-(1-piperazinylcarbonyl)oxindol hydrochloride, and 1.5 ml of triethylamine, and the mixture was reacted at room temperature for 3 hours. After completion of reaction, DMF was distilled off under reduced pressure, and the residue was washed with water. The resultant residue was purified by silica-gel column chromatography (eluent: dichloromethane:methanol=100:5). By recrystallization from a mixture of methanol and dichloromethane, 0.4 g of 5-[4-(2-benzoylethyl)-1-piperazinylcarbonyl]oxindol was obtained.

m.p.: 208°-210° C.
Colorless prisms

EXAMPLE 26

5-(1-Piperazinylcarbonyl)oxindol hydrochloride (1.0 g), 1.2 g of DBU, and 0.73 g of isobutyl bromide were suspended in 15 ml of acetonitrile and the suspension was reflexed for 6 hours. To the mixture were then added 0.6 ml of triethylamine and 0.73 g of isobutyl bromide and the mixture was further reflexed for 8 hours. The reaction mixture was poured into a saturated aqueous solution of sodium hydrogencarbonate and extracted with chloroform. The chloroform layer was washed with a saturated saline solution and dried over sodium sulfate. The residue obtained after the solvent was distilled off was purified by silica-gel column chromatography (eluent: dichloromethane:methanol=20:1). The product was converted into the hydrochloride with acetone and hydrochloricacid, and recrystallized from a mixture of ethanol and methanol to give 0.39 g of 5-(4-isobutyl-1-piperazinylcarbonyl)oxindol hydrochloride.

m.p.: 285°-289° C. (decomposed)
Colorless needles

EXAMPLE 27

In an analogous manner as Examples 25 or 26, the same compounds as those obtained in Examples 20 and 22 and Example 31 given below were prepared using appropriate starting materials.

EXAMPLE 28

5-(α-Chloroacetyl)oxindol (1.0 g), 1.2 g of 3,4-dimethoxybenzoyl-l-piperazine, and 0.8 ml of triethylamine were suspended in 10 ml of acetonitrile, and the suspension was stirred at room temperature for 17 hours. Insoluble matters were filtered off. The filtrate was concentrated, added to a saturated aqueous solution of sodium hydrogencarbonate, and extracted with chloroform. The chloroform layer was washed with water and saturated saline solution, in turn, dried over anhydrous sodium sulfate, and the solvent was distilled off under reduced pressure. The residue was purified by silica-gel column chromatography (eluent: chloroform:methanol=20:1). It was converted into the hydrochloride with methanol and conc. hydrochloric acid. Recrystallization from a mixture of ethanol and methanol gave 0.34 g of 5-[2-[4-(3,4-dimethoxybenzoyl)-1-piperazinyl]acetyl]oxindol hydrochloride.

m.p.: 218°-221° (decomposed)
Pale yellow needles

In an analogous manner as Example 28, the compounds shown in Table 3 were prepared using appropriate starting materials.

TABLE 3

| Example | (A)$_n$ | R | Crystal Form (Recrystallization solvent) | m.p. (°C.) | Salt |
|---|---|---|---|---|---|
| 29 | —CH$_2$— | —CO—C$_6$H$_4$—CH$_3$ | Pale-yellow needles (methanol-ethanol) | 242-245 (decomposed) | ¼H$_2$O |
| 30 | —CH$_2$— | —CO—C$_6$H$_3$(OCH$_2$O) (methylenedioxybenzoyl) | Colorless prisms (methanol-ethanol) | 202-205 (decomposed) | HCl |
| 31 | —CH$_2$— | —CH$_2$—C$_6$H$_5$ | (Colorless powdery crystal) (methanol) | 183-187 (decomposed) | 2HCl.H$_2$O |
| 32 | —CH$_2$— | —COCH$_3$ | Colorless needles (ethanol-water) | 248-251 (decomposed) | HCl.½H$_2$O |

TABLE 3-continued structure: CO—(A)ₙ—N⌒N—R (piperazine) attached to 5-position of oxindole (indolin-2-one)

| Example | (A)ₙ | R | Crystal Form (Recrystallization solvent) | m.p. (°C.) | Salt |
|---|---|---|---|---|---|
| 33 | —CH$_2$— | —CO—(phenyl with OCH$_3$, OCH$_3$, OCH$_3$) | Pale-yellow needles (methanol-ethanol) | 211–214 | |
| 34 | —CH$_2$— | H | Colorless prisms (methanol-water) | 232–235 (decomposed) | 2HCl |
| 35 | —CH$_2$— | —CO—(phenyl with Cl) | Pale-yellow prisms (ethanol-chloroform) | 215–218 (decomposed) | — |
| 36 | —CH$_2$— | —CO—(phenyl) | Colorless powdery crystal (ethanol-water) | 145–150 (decomposed) | HCl.2H$_2$O |

EXAMPLE 37

To a suspension comprising 1.0 g of dihydrochloric acid salt of 5-[2-(1-piperazinyl)acetyl]oxindol, 0.63 g of potassium carbonate, 5 ml of water and 10 ml of acetone was added dropwise a solution of 0.63 g of m-chlorobenzoyl chloride in 2 ml of acetone under ice-cooling with stirring, and the mixture was stirred for 1.5 hours at the same temperature. After completion of reaction, the reaction mixture was poured into ice-water and extracted with chloroform. The chloroform layer was washed, in turn, with water and a saturated saline solution, and dried over sodium sulfate. The solvent was then distilled off under reduced pressure. The resultant residue was purified by silica-gel column chromatography (eluent: chloroform:methanol=20:1) and recrystallized from a mixture of ethanol and chloroform to give 0.34 g of 5-[2-[4-(3-chlorobenzoyl)-1-piperazinyl]acetyl]oxindol.

m.p.: 215°–218° C. (decomposed)
Pale yellow prisms

EXAMPLE 38

In an analogous manner as Example 37, the same compounds as those obtained in Examples 28 to 30, 32, 33 and 36 was prepared using appropriate starting materials.

EXAMPLE 39

5[2-(4-Benzyl-1-piperazinyl)acetyl]oxindol (11 g) and 1 g of 10% Pd-C were suspended in a mixed solvent of 100 ml ethanol and 5 ml water and the suspension was subjected to hydrogenolysis under atmospheric pressure at room temperature. After completion of reaction, the catalyst was filtered off and the filtrate was concentrated. The resultant residue was converted into its hydrochloride according to a conventional manner and recrystallized from a mixture of methanol and water to give 4.0 g of 5-[2-(1-piperazinyl)acetyl]-oxindol dihydrochloride. Colorless prisms m.p.: 232°–235° C.

EXAMPLE 40

In an analogous manner as Example 39, the same compound as that obtained in Example 16 was prepared using appropriate starting materials.

EXAMPLE 41

5-Carboxyoxindol (0.93 g), 1.3 g of DCC, and 1.1 g of benzylpiperazine were suspended in 10 ml of dioxane, and the suspension was stirred at 60° to 70° C. for 5 hours. After completion of reaction, the solvent was distilled off and ethyl ether was added to the residue and crystals which precipitated were filtered off. After concentrating the filtrate, the residue was dissolved with an addition of chloroform. The solution was washed with water and a saturated saline solution. After drying over anhydrous sodium sulfate, the solvent was distilled off. The residue were recrystallized from isopropyl alcohol to give 300 mg of 5-(4-benzyl-1-piperazinylcarbonyl)oxindol.

m.p.: 151°–153° C.
Colorless prisms

EXAMPLE 42

In an analogous manner as Example 41, the same compounds as those obtained in Examples 16 to 22 were prepared using appropriate starting materials.

EXAMPLE 43

5-Carboxyoxindol (0.93 g) and 0.8 ml of trimethylamine were suspended in 10 ml of tetrahydrofuran (THF), and a solution of 1.0 g of diethylchlorophosphate in 10 ml of THF was added dropwise thereto at room temperature with stirring. The mixture was stirred for 3 hours at room temperature. To the mixture was added dropwise a solution of 1.1 g of benzylpiperazine in 10 ml of THF and was further stirred for 10 hours at room temperature. After completion of reaction, crystals which precipitated were filtered off and the filtrate was concentrated. To the residue was added a saturated aqueous solution of sodium hydrogencarbonate and the mixture was extracted with chloroform. Organic layer was washed with water and a saturated saline solution, dried over anhydrous sodium sulfate, and the solvent was distilled off. Recrystallization of the residue from isopropyl alcohol gave 1.01 g of 5-(4-benzyl-1-piperazinylcarbonyl)oxindol.

m.p.: 151°–153° C.

Colorless prisms

EXAMPLE 44

In an analogous manner as Example 43, the same compounds as those obtained in Examples 16 to 22 were prepared using appropriate starting materials.

EXAMPLE 45

To a suspension of 1.76 g of 5-carboxyoxindol in 200 ml of methylene chloride was added 2 ml of pyridine. After completion of addition, to the suspension was added dropwise 1.4 g of thionyl chloride with stirring held at 0° to 20° C. After completion of addition, the mixture was stirred at the same temperature for 1 hour, and a solution of 1.74 g of benzylpiperazine in 10 ml of methylene chloride was added dropwise thereto. The mixture was then stirred for 4 hours at room temperature. The reaction mixture was thoroughly washed with an aqueous potassium carbonate solution, then washed with water, and dilute hydrochloric acid, dried over sodium sulfate, and the solvent was distilled off. The residue was isolated and purified by silica-gel column chromatography [silica-gel: WAKO C-200, eluent: chloroform:methanol (V/V)=20:1] followed by recrystallization from isopropyl alcohol to give 298 mg of 5-(4-benzyl-1-piperazinylcarbonyl)oxindol.

m.p.: 151°–153° C.

Colorless prisms

In an analogous manner as Example 45, the same compounds as those obtained in Examples 16 to 22 were prepared using appropriate starting materials.

EXAMPLE 46

To a solution of 3.2 g of benzoic acid and 4 ml of triethylamine in 50 ml of DMF was added dropwise a solution of 3.87 g of isobutyl chloroformate in 2 ml of DMF. After stirring the mixture for 30 minutes at room temperature, a solution of 8.8 g of 5-(1-piperazinylcarbonyl)oxindol in 3 ml of DMF was added dropwise thereto, and the mixture was stirred for 30 minutes at room temperature and then for 1 hour at 50° to 60° C. The reaction mixture was poured into a large amount of a saturated saline solution, extracted with chloroform, washed with water and dried. The solvent was distilled off, and the residue was recrystallized from methanol to give 1.9 g of 5-(4-benzoyl-1-piperazinylcarbonyl)oxindol.

m.p. 268°–270° C.

Colorless prisms

In an analogous manner as Example 46, the same compounds as those obtained in Examples 17, 28 to 30, 32, 33, 35 and 36 were prepared using appropriate starting materials.

EXAMPLE 47

To 100 ml of ethanol were added 1.36 g of ethyl benzoate, 0.5 g of sodium ethylate and 2.6 g of 5-(piperazinylcarbonyl)oxindol hydrochloride and the mixture was reacted in an autocrave at 140° to 150° C. under 110 atm for 6 hours. After cooling, the reaction mixture was concentrated under reduced pressure and the residue was dissolved in 200 ml of chloroform. After washing, in turn, with 1% aqueous potassium carbonate solution, dilute hydrochloric acid, and water, the chloroform solution was dried over anhydrous sodium sulfate and the solvent was distilled off. The resultant residue was purified by silica-gel column chromatography [silica-gel: WAKO C-200, eluent: chloroform:methanol (V/V)=20:1], and the crude crystal was recrystallized from methanol to give 215 mg of 5-(4-benzoyl-1-piperazinylcarbonyl)oxindol.

m.p.: 268°–270° C.

Colorless prisms

In an analogous manner as Example 47, the same compounds as those obtained in Examples 17, 28 to 30, 32, 33, 35 and 36 were prepared using appropriate starting materials.

EXAMPLE 48

To a mixed solvent of 20 ml of dioxane and 20 ml of methylene chloride were added 1.2 g of benzoic acid and 3.0 g of 5-(1-piperazinylcarbonyl)oxindol hydrochloride. To this mixture, a solution of 2.1 g of N,N-dicyclohexylcarbodiimide dissolved in 5 ml of methylene chloride was added dropwise at 10° to 20° C. under ice-cooling externally with stirring. Then, the mixture was stirred for 3.5 hours at the same temperature. Crystals which precipitated were filtered off, and the filtrate was concentrated to dryness under reduced pressure. The resultant residue was dissolved in 100 ml of methylene chloride, and the organic layer was washed, in turn, with 5% aqueous hydrochloric acid solution, 5% aqueous sodium hydrogen carbonate solution, and water, and dried over anhydrous sodium sulfate. Under reduced pressure, the solvent was distilled off and the residue was recrystallized from methanol to give 0.79 g of 5-(4-benzoyl-1-piperazinylcarbonyl)oxindol.

m.p.: 268°–270° C.

Colorless prisms

In an analogous manner as Example 48, the same compounds as those obtained in Examples 17, 28 to 30, 32, 33, 35 and 36 were prepared using appropriate starting materials.

PHARMACOLOGICAL TESTS

Pharmacological activity of the compounds of this invention was determined as described below.

Isolated Blood-Perfused Papillary Muscle Preparations

Experiments were carried out on adult mongrel dogs of either sex. The papillary muscle preparations were obtained from dogs weighing 8–13 kg, anesthetized with pentobarbital sodium (30 mg/kg i.v.), given heparin sodium (1000 U/kg i.v.) and exsanguinated. The preparation was essentially the anterior papillary muscle excised together with the ventricular septum and was set up in cold Tyrode's solution. The preparation was placed in a glass water jacket maintained at about 38° C. and cross-circulated through the cannulated anterior septal artery with blood from a donor dog at a constant pressure of 100 mmHg. Dogs used as donors were 18–27 kg in body weight and were anesthetized with pentobarbital sodium (30 mg/kg i.v.). Heparin sodium was given at a dose of 1000 U/kg i.v. The papillary muscle was driven with rectangular pulse about 1.5 times the threshold voltage (0.5–3 V) and 5 msec duration at a fixed rate of 120 beats/min. through bipolar pacing electrodes. Tension developed by the papillary muscle was measured with a strain-gauge transducer. The muscle was loaded with a weight of about 1.5 g. Blood flow through the anterior septal artery was measured by an electromagnetic flow meter. Recording of developed tension and blood flow was made on charts with an ink-writing rectigraph. Details of the preparation have been described by Endoh and Hashimoto (*Am. J. Physiol.* 218, 1459–1463, 1970). The compounds in volumes of 10–30 μl were injected intraarterially in 4 sec. The inotropic effects of the compounds are expressed as a percentage of the developed tension before the injection of the compounds. The effects of the compounds on blood flow are expressed as difference (ml/min.) between the values before and after the injection of the compounds. The results are obtained are shown in Table 4 below.

Test compounds
1. 5-[4-(3,4-Dimethoxybenzoyl)-1-piperazinyl]oxindol
2. 5-[4-(4-Ethoxybenzoyl)-1-piperazinyl]oxindol
3. 5-(4-Ethoxycarbonyl-1-piperazinyl)oxindol
4. 5-[4-(4-Methylbenzoyl)-1-piperazinyl]oxindol
5. 5-(4-Benzyl-1-piperazinyl)oxindol
6. 5-(4-Isobutyl-1-piperazinylcarbonyl)oxindol hydrochloride
7. 5-[4-(2-Phenoxyethyl)-1-piperazinylcarbonyl]oxindol
8. 5-[2-[4-(3,4-Dimethoxybenzoyl)-1-piperazinyl]acetyl]oxindol hydrochloride
9. 5-[2-(4-Benzyl-1-piperazinyl)acetyl]oxindol dihydrochloride-monohydrate
10. 5-[2-[4-(3,4-Methylenedioxybenzoyl)-1-piperazinyl]acetyl]oxindol hydrochloride
11. 5-[2-[4-(4-Methylbenzoyl)-1-piperazinyl]acetyl]oxindol 1/4 hydrate
12. 5-[2-[4-(3-Chlorobenzoyl)-1-piperazinyl]acetyl]oxindol

TABLE 4

| Test Compound | Dose (μ mole) | % Change in Contraction of Papillary Muscle | Change in Rate of Coronary Blood Flow (ml/min.) |
|---|---|---|---|
| 1 | 1 | 12 | 1.0 |
| 2 | 1 | 17 | 1.5 |
| 3 | 1 | 25 | 1.5 |
| 4 | 1 | 9 | — |
| 5 | 1 | 15 | 1.5 |
| 6 | 1 | 15 | 1.0 |
| 7 | 1 | 32 | 1.5 |
| 8 | 1 | 6 | 2.0 |
| 9 | 1 | 8 | 1.75 |
| 10 | 1 | 10 | — |
| 11 | 0.3 | 7 | 0.5 |
| 12 | 1 | 20 | — |

PREPARATION EXAMPLE 1

| | |
|---|---|
| 5-[4-(3,4-Dimethoxybenzoyl)-1-piperazinyl]oxindol | 5 mg |
| Starch | 132 mg |
| Magnesium stearate | 18 mg |
| Lactose | 45 mg |
| Total | 200 mg |

Tablets each having the above composition were prepared in a conventional manner.

PREPARATION EXAMPLE 2

| | |
|---|---|
| 5-[4-(4-Ethoxybenzoyl)-1-piperazinyl]oxindol | 10 mg |
| Starch | 127 mg |
| Magnesium stearate | 18 mg |
| Lactose | 45 mg |
| Total | 200 mg |

Tablets each having the above composition were prepared in a conventional manner.

PREPARATION EXAMPLE 3

| | |
|---|---|
| 5-[4-(4-Methylbenzoyl)-1-piperazinyl]oxindol | 500 mg |
| Polyethylene glycol (molecular weight: 4,000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the distilled water at 80° C. while stirring. The resulting solution was cooled to 40° C. and the compound of the invention, polyethylene glycol and polyoxyethylene sorbitan monooleate were dissolved therein. Then, distilled water for injection was added to adjust the volume to final one. The mixture was filtered using a suitable filter paper to sterilize and then filled in an ampoule of 1 ml, thus forming preparation for injection.

PREPARATION EXAMPLE 4

| | |
|---|---|
| 5-[4-(3,4,5-Trimethoxybenzoyl)-1-piperazinyl]oxindol | 5 mg |
| Starch | 132 mg |
| Magnesium stearate | 18 mg |
| Lactose | 45 mg |
| Total | 200 mg |

Tablets each having the above composition were prepared in a conventional manner.

PREPARATION EXAMPLE 5

| 5-[2-[4-(3,4-Dimethoxybenzoyl)- 1-piperazinyl]acetyl]oxindol | 5 mg |
|---|---|
| Starch | 132 mg |
| Magnesium stearate | 18 mg |
| Lactose | 45 mg |
| Total | 200 mg |

Tablets each having the above composition were prepared in a conventional manner.

PREPARATION EXAMPLE 6

| 5-(4-Benzoyl-1-piperazinyl- carbonyl)oxindol | 10 mg |
|---|---|
| Starch | 127 mg |
| Magnesium stearate | 18 mg |
| Lactose | 45 mg |
| Total | 200 mg |

Tablets each having the above composition were prepared in a conventional manner.

PREPARATION EXAMPLE 7

| 5-[2-[4-Methylbenzoyl)- 1-piperazinyl]acetyl]oxindol | 500 mg |
|---|---|
| Polyethylene glycol (molecular weight: 4,000) | 0.3 g |
| Sodium chloride | 0.9 g |
| Polyoxyethylene sorbitan monooleate | 0.4 g |
| Sodium Metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the distilled water at 80° C. while stirring. The resulting solution was cooled to 40° C. and the compound of the invention polyethylene glycol and polyoxyethylene sorbitan monooleate were dissolved therein. Then, distilled water for injection was added to adjust the volume to final one. The mixture was filtered using a suitable filter paper to sterilize and then filled in an ampoule of 1 ml, thus forming preparation for injection.

PREPARATION EXAMPLE 8

| 5-[4-(2-Phenoxyethyl)- 1-piperazinylcarbonyl]oxindol | 5 mg |
|---|---|
| Starch | 132 mg |
| Magnesium stearate | 18 mg |
| Lactose | 45 mg |
| Total | 200 mg |

Tablets each having the above composition were prepared in a conventional manner.

While the invention has been described in detail and with reference to specific embodiments thereof, it will be apparent to one skilled in the art that various changes and modifications can be made therein without departing from the spirit and scope thereof.

What we claim is:

1. An oxindol compound of the formula:

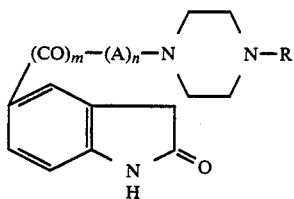

wherein

A is a $C_1$-$C_6$ alkylene group;

R is a $C_1$-$C_6$ alkyl group, a phenyl-$C_1$-$C_6$ alkyl group, a phenoxy-$C_1$-$C_6$ alkyl group, a benzoyl-$C_1$-$C_6$ alkyl group, a $C_1$-$C_6$ alkoxycarbonyl group, a benzoyl group which may be substituted with a $C_1$-$C_6$ alkyl group, 1 to 3 of a $C_1$-$C_6$ alkoxy group or a halogen atom on the benzene ring thereof, or a benzoyl group which is substituted with a $C_1$-$C_4$ alkylenedioxy group on the benzene ring thereof; and m and n, which may be the same or different, is an integer of 0 or 1, with the proviso that when n is 1, then m is 1, and when A is an ethylene group and m is 1, then R is not a 3,4,5-trimethoxybenzoyl group, and pharmaceutically acceptable salts thereof.

2. The oxindol compound of claim 1, wherein n is 0.

3. The oxindol compound of claim 2, wherein m is 1.

4. The oxindol compound of claim 3, wherein R is a $C_1$-$C_6$ alkyl group, a phenyl-$C_1$-$C_6$ alkyl group, a phenoxy-$C_1$-$C_6$ alkyl group, a benzoyl-$C_1$-$C_6$ alkyl group, or a $C_1$-$C_6$ alkoxycarbonyl group.

5. The oxindol compound of claim 4, wherein R is a benzoyl-$C_1$-$C_6$ alkyl group.

6. The oxindol compound of claim 3, wherein R is a benzoyl group which may be substituted with a $C_1$-$C_6$ alkyl group, 1 to 3 of a $C_1$-$C_6$ alkoxy group or a halogen atom on the benzene ring thereof, or a benzoyl group which is substituted with a $C_1$-$C_4$ alkylenedioxy group on the benzene ring thereof.

7. The oxindol compound of claim 2, wherein m is 0.

8. The oxindol compound of claim 7, wherein R is a benzoyl group which may be substituted with a $C_1$-$C_6$ alkyl group, 1 to 3 of a $C_1$-$C_6$ alkoxy group or a halogen atom on the benzene ring thereof, or a benzoyl group which is substituted with a $C_1$-$C_4$ alkylenedioxy group on the benzene ring thereof.

9. The oxindol compound of claim 8, wherein R is a benzoyl group which is substituted with 1 to 3 of a $C_1$-$C_6$ alkoxy group on the benzene ring thereof or with a $C_1$-$C_4$ alkylenedioxy group on the benzene ring thereof.

10. The oxindol compound of claim 9, wherein R is a benzoyl group which is substituted with 1 to 3 of a methoxy group.

11. The oxindol compound of claim 7, wherein R is a $C_1$-$C_6$ alkyl group, a phenyl-$C_1$-$C_6$ alkyl group, a phenoxy-$C_1$-$C_6$ alkyl group, a benzoyl-$C_1$-$C_6$ alkyl group or a $C_1$-$C_6$ alkoxycarbonyl group.

12. The oxindol compound of claim 1, wherein n is 1.

13. The oxindol compound of claim 12, wherein R is a benzoyl group which may be substituted with a $C_1$-$C_6$ alkyl group, 1 to 3 of a $C_1$-$C_6$ alkoxy group or a halgen atom on the benzene ring thereof, or a benzoyl group which is substituted with a $C_1$-$C_4$ alkylenedioxy group on the benzene ring thereof.

14. The oxindol compound of claim 12, wherein R is a $C_1$–$C_6$ alkyl group, a phenyl-$C_1$–$C_6$ alkyl group, a phenoxy-$C_1$–$C_6$ alkyl group, a benzoyl-$C_1$–$C_6$ alkyl group, or a $C_1$–$C_6$ alkoxycarbonyl group.

15. The oxindol compound of claim 5 which is 5-[4-(2-Benzoylethyl)-1-piperazinyl-carbonyl]oxindol.

16. The oxindol compound of claim 4 which is 5-[4-(2-Phenoxyethyl)-1-piperazinyl-carbonyl]oxindol.

17. The oxindol compound of claim 10 which is 5-[4-(3,4-Dimethoxybenzoyl)-1-piperazinyl]-oxindol.

18. The oxindol compound of claim 9 which is 5-[4-(4-Ethoxybenzoyl)-1-piperazinyl]-oxindol.

19. The oxindol compound of claim 8 which is 5-[4-(4-Methylbenzoyl)-1-piperazinyl]-oxindol.

20. The oxindol compound of claim 11 which is 5-(4-Ethoxycarbonyl-1-piperazinyl)oxindol.

21. The oxindol compound of claim 11 which is 5-(4-Benzyl-1-piperazinyl)oxindol.

22. A cardiotonic composition comprising a cardiotonically effective amount of a compound of the formula:

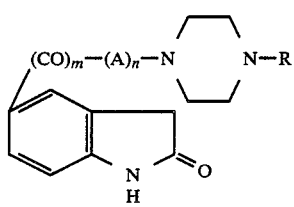

(I)

wherein

A is a $C_1$–$C_6$ alkylene group;

R is a $C_1$–$C_6$ alkyl group, a phenyl-$C_1$–$C_6$ alkyl group, a phenoxy-$C_1$–$C_6$ alkyl group, a benzoyl-$C_1$–$C_6$ alkyl group, a $C_1$–$C_6$ alkoxycarbonyl group, a benzoyl group which may be substituted with a $C_1$–$C_6$ alkyl group, 1 to 3 of a $C_1$–$C_6$ alkoxy group or a halogen atom on the benzene ring thereof, or a benzoyl group which is substituted with a $C_1$–$C_4$ alkylenedioxy group on the benzene ring thereof; and m and n, which may be the same or different, is an integer of 0 to 1, with the proviso that when n is 1, then m is 1, and when A is an ethylene group and m is 1, then R is not a 3,4-5-trimethoxybenzoyl group, and pharmaceutically acceptable salts thereof and a pharmaceutically acceptable carrier therefor.

23. A method for treatment of congestive heart failure which comprises adminstering to a human being or animal a compound of the formula:

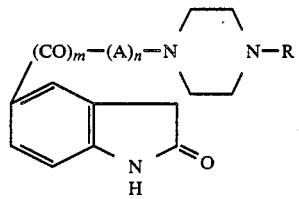

wherein

A is a $C_1$–$C_6$ alkylene group;

R is a $C_1$–$C_6$ alkyl group, a phenyl-$C_1$–$C_6$ alkyl group, a phenoxy-$C_1$–$C_6$ alkyl group, a benzoyl-$C_1$–$C_6$ alkyl group, a $C_1$–$C_6$ alkoxycarbonyl group, a benzoyl group which may be substituted with a $C_1$–$C_6$ alkyl group, 1 to 3 of a $C_1$–$C_6$ alkoxy group or a halogen atom on the benzene ring thereof, or a benzoyl group which is substituted with a $C_1$–$C_4$ alkylenedioxy group on the benzene ring thereof; and m and n, which may be the same or different, is an integer of 0 to 1, with the proviso that when n is 1, then m is 1, and when A is an ethylene group and m is 1, then R is not a 3,4-5-trimethoxybenzoyl group, and pharmaceutically acceptable salts thereof.

24. The oxindol compound of claims 4, 11 or 14, wherein R is a $C_1$–$C_6$ alkyl group, a phenoxy-$C_1$–$C_6$ alkyl group, a benzoyl-$C_1$–$C_6$ alkyl group or a $C_1$–$C_6$ alkoxy-carbonyl group.

25. The oxindol compound of claims 6, 8 or 13, wherein R is a benzoyl group which may be substituted with 1 to 3 of a $C_1$–$C_6$ alkoxy group or a halogen atom on the benzene ring thereof, or a benzoyl group which is substituted with a $C_1$–$C_4$ alkylenedioxy group on the benzene ring thereof.

* * * * *